(12) United States Patent
Choi et al.

(10) Patent No.: US 10,260,035 B2
(45) Date of Patent: Apr. 16, 2019

(54) CELL STIMULATING SYSTEM

(71) Applicant: Daegu Gyeongbuk Institute of Science and Technology, Daegu (KR)

(72) Inventors: Hong Soo Choi, Daegu (KR); Won Jun Lee, Uijeongbu-si (KR); Joon Taek Jung, Daegu (KR)

(73) Assignee: Daegu Gyeongbuk Institute of Science and Technology, Dalseong-Gun (KR)

( * ) Notice: Subject to any disclaimer, the term of this patent is extended or adjusted under 35 U.S.C. 154(b) by 3 days.

(21) Appl. No.: 15/306,660

(22) PCT Filed: Nov. 18, 2014

(86) PCT No.: PCT/KR2014/011063
§ 371 (c)(1),
(2) Date: Oct. 25, 2016

(87) PCT Pub. No.: WO2015/167097
PCT Pub. Date: Nov. 5, 2015

(65) Prior Publication Data
US 2017/0058250 A1    Mar. 2, 2017

(30) Foreign Application Priority Data

Apr. 30, 2014    (KR) ........................ 10-2014-0052587

(51) Int. Cl.
*C12M 1/42* (2006.01)
*C12N 13/00* (2006.01)
*C12M 1/00* (2006.01)

(52) U.S. Cl.
CPC ............ *C12M 35/04* (2013.01); *C12M 23/58* (2013.01); *C12N 13/00* (2013.01)

(58) Field of Classification Search
CPC .................................................. C12M 35/04
(Continued)

(56) References Cited

U.S. PATENT DOCUMENTS

2006/0236747 A1* 10/2006 Greenleaf .......... A61H 23/0236
                                                         73/1.82
2007/0299539 A1    12/2007 Othman et al.
(Continued)

FOREIGN PATENT DOCUMENTS

JP    2005-080606 A    3/2005
JP    2005-160340 A    6/2005
(Continued)

OTHER PUBLICATIONS

Jung et al., Fabrication of a two-dimensional piezoelectric micromachined ultrasonic transducer array using a top-crossover-to-bottom structure and metal bridge connections, Nov. 15, 2013, Journal of Micromechanics and Microengineering, vol. 23 No. 12.*
(Continued)

*Primary Examiner* — Kevin Joyner
*Assistant Examiner* — Holly M Mull
(74) *Attorney, Agent, or Firm* — Gregory L. Ozga; Warn Partners, P.C.

(57) ABSTRACT

Provided is a cell stimulating system including an oscillator, in an ultrasound probe array type, including a plurality of ultrasound devices disposed in a matrix structure, the oscillator being produced using a micro electro mechanical system (MEMS), a plurality of cell containers configured to each contain a cell that is selectively stimulated by the ultrasound devices, the cell containers being disposed on a top of the oscillator to correspond to each of the ultrasound devices, and a device operator configured to operate an ultrasound device selected from among the ultrasound devices.

7 Claims, 4 Drawing Sheets

(58) Field of Classification Search
USPC .................................................. 435/305.2
See application file for complete search history.

(56) References Cited

U.S. PATENT DOCUMENTS

| | | | | |
|---|---|---|---|---|
| 2015/0265245 | A1* | 9/2015 | von Ramm | ......... G01S 7/52017 600/443 |
| 2015/0376562 | A1* | 12/2015 | Baum | ....................... B01L 9/06 435/304.1 |

FOREIGN PATENT DOCUMENTS

| | | | |
|---|---|---|---|
| JP | 2008-035834 A | 2/2008 |
| KR | 10-2009-0008784 A | 1/2009 |
| KR | 10-1126599 B1 | 3/2012 |
| KR | 10-1327209 B1 | 11/2013 |

OTHER PUBLICATIONS

International Search Report for International Application No. PCT/KR2014/011063 filed on Nov. 18, 2014.
IEEE Trans. Ultrason. Ferroelectr. Freq. Control, vol. 58, pp. 1266-1271 (2011).
International Search Report for International Application No. PCT/KR2014/011063.

* cited by examiner

1

100

CELL STIMULATING SYSTEM

This application is a National Stage of International Application No. PCT/KR2014/011063, filed Nov. 18, 2014. This application claims priority to Korean Patent Application No. KR 10-2014-0052587 filed on Apr. 30, 2014. The disclosure(s) of the above application(s) is (are) incorporated herein by reference.

TECHNICAL FIELD

The present invention relates to a cell stimulating system, and more particularly, to a cell stimulating system for selectively and simultaneously stimulating a cell of a cell container based on a plurality of parameters through selective operations of a plurality of ultrasound devices by a device operator.

BACKGROUND ART

Cells included in mechanical response tissues of humans and animals are exposed to various mechanical stimulations, such as a tensile force, a shearing force, and a compressive force. Repeated mechanical stimulations may cause a disease, such as arthritis, affecting articular cartilage tissue. Accordingly, research being conducted on cell responses caused by the mechanical stimulations has been receiving attention.

When replacement tissues, mechanical response tissues in particular, for humans and animals are developed to have complete functions from stem cells, mechanical stimulations are applied to cells while the stem cells are being grown. A level of stimulations applied to the cells may vary based on a type of cell and a type of tissue being developed.

Research is being done on cell response and cell stimulation for developing stem cells. For example, Korean Patent Laid-Open Publication No. 10-2011-0059186 discloses a once-through ultrasound stimulating culture system for an adult stem cell, and Korean Patent Laid-Open Publication No. 10-2007-0072023 discloses a method of effectively separating and multiplying a mesenchyma stem cell from a tissue and a cell using an ultrasound of low intensity.

FIG. 1 is a diagram illustrating a cell stimulation apparatus according to related art.

Referring to FIG. 1, a related cell stimulation apparatus 1 includes a plurality of ultrasound transducers, for example, an ultrasound transducer 10, a plurality of cell containing tubes, for example, a cell containing tube 20, disposed on a top of each of the ultrasound transducers.

In a case of such configuration, because a cell is put in the tube 20 to stimulate the cell through the ultrasound transducer 10, the configuration may be used when culturing the cell in a condition in which the cell floats. The configuration may be limitedly used in a condition in which the cell is at a bottom of the tube, due to a spatial limitation that exists when stimulating the cell in such condition. Also, because an intensity of an ultrasound wave being transmitted is decreased due to a thick base of the cell containing tube 20, it may be difficult to accurately estimate the intensity of the ultrasound wave to be used for stimulation.

Research on disposing an ultrasound transducer inside of a cell containing tube has been conducted, but with such configuration a size and complexity of an entire apparatus may increase. Thus, a plurality of ultrasound transducers corresponding to the cell containing tubes may be requested in order to stimulate cells by changing a stimulating time, a frequency of an ultrasound wave, and an availability rate.

DISCLOSURE OF INVENTION

Technical Goals

An aspect of the present invention is to provide a cell stimulating system for selectively and simultaneously stimulating a cell of a cell container based on a plurality of parameters by selective operation of a plurality of ultrasound devices by a device operator such that various experiments are simultaneously performed while cost and an amount of time used for the experiments are reduced.

Another aspect of the present invention is to provide a cell stimulating system for using an ultrasound probe array to which a micro electro mechanical system (MEMS) is applied such that a size of an apparatus is minimized when compared to that of a related system, wherein a cell experiment is performed in an incubator thereby increasing a reliability of the experiment.

Still another aspect of the present invention is to provide a cell stimulating system that enables an experimenter to perform an experiment based on a desired intensity of an ultrasound wave in a structure in which a cell container transmits the ultrasound wave in lieu of decreasing an intensity of the ultrasound wave.

Technical Solutions

According to an aspect of the present invention, there is provided a cell stimulating system including an oscillator, in an ultrasound probe array type, including a plurality of ultrasound devices disposed in a matrix structure, the oscillator being produced using a micro electro mechanical system (MEMS), a plurality of cell containers configured to each contain a cell that is selectively stimulated by the ultrasound devices, the cell containers being disposed on a top of the oscillator to correspond to each of the ultrasound devices, and a device operator configured to operate an ultrasound device selected from among the ultrasound devices, wherein the cell of each of the cell containers is selectively and simultaneously stimulated based on a plurality of parameters, by selective operation of the ultrasound devices of the oscillator by the device operator, such that various experiments are simultaneously performed while cost and an amount of time used for the experiments are reduced.

The ultrasound devices may be arranged in a polygonal shape, a circular shape, or an oval shape, and the device operator is configured to selectively operate the ultrasound devices such that an alternating current (AC) voltage having a resonance frequency of each of the ultrasound devices is applied to ultrasound devices disposed in one direction of the oscillator, and ultrasound devices disposed in another direction of the oscillator are used as grounds.

The oscillator may include a printed circuit board on which the ultrasound devices are disposed, and an electrode configured to transmit a current to be applied to each of the ultrasound devices, the electrode being included in the printed circuit board to correspond to each of the ultrasound devices.

Each of the cell containers may include a cell culture dish configured to contain the cell, the cell culture dish being disposed on a top of each of the ultrasound devices, and a dish holder configured to hold the cell culture dish such that a bottom of the cell culture dish is adjacent to each of the ultrasound devices.

The cell culture dish may hang on a top of the dish holder such that the cell culture dish is disposed on the top of each of the ultrasound devices.

The dish holder may be formed to have an open bottom such that the cell culture dish is in contact with each of the ultrasound devices.

The cell of each of the cell containers may be selectively and simultaneously stimulated based on a plurality of parameters, by selective operation of the ultrasound devices of the oscillator by the device operator.

Effects

According to an embodiment of the present invention, it is possible to selectively and simultaneously stimulate a cell of a cell container based on a plurality of parameters, by selective operation of a plurality of ultrasound devices of an oscillator by a device operator, such that various experiments are simultaneously performed while cost and an amount of time used for the experiments are reduced.

According to another embodiment of the present invention, it is possible to use an ultrasound probe array to which a micro electro mechanical system (MEMS) is applied such that a size of an apparatus is minimized when compared to that of a related system, wherein a cell experiment is performed in an incubator thereby increasing a reliability of the experiment.

According to still another embodiment of the present invention, it is possible to enable an experimenter to perform an experiment based on a desired intensity of an ultrasound wave in a structure in which a cell container transmits the ultrasound wave in lieu of decreasing an intensity of the ultrasound wave.

BEST MODE FOR CARRYING OUT THE INVENTION

Figure 1:
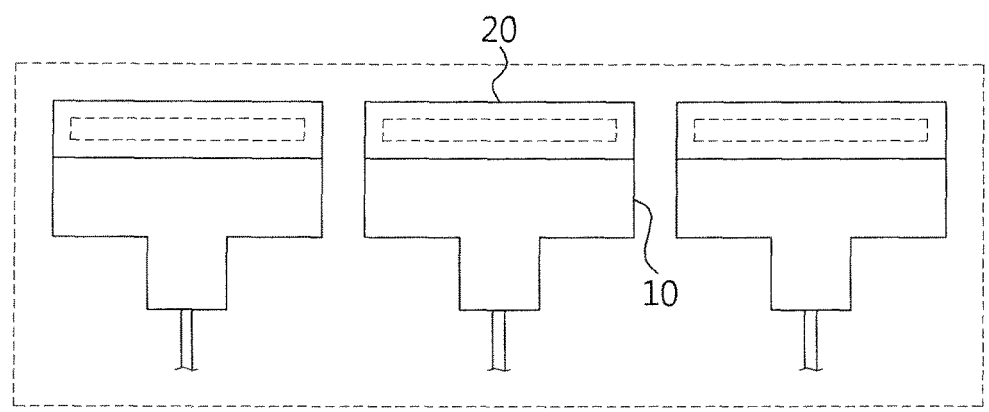
FIG. 1 is a diagram illustrating a cell stimulation apparatus according to related art.

Reference will now be made in detail to example embodiments of the present invention, examples of which are illustrated in the accompanying drawings, wherein like reference numerals refer to the like elements throughout. The embodiments are described below in order to explain the present invention by referring to the figures. The following description is one of diverse aspects of the present invention which can be claimed for a patent and constitutes part of the detailed description of the present invention.

In describing the present invention, detailed descriptions related to a known function or configuration will be omitted herein so as to clarify the substance of the present invention.

Figure 2:
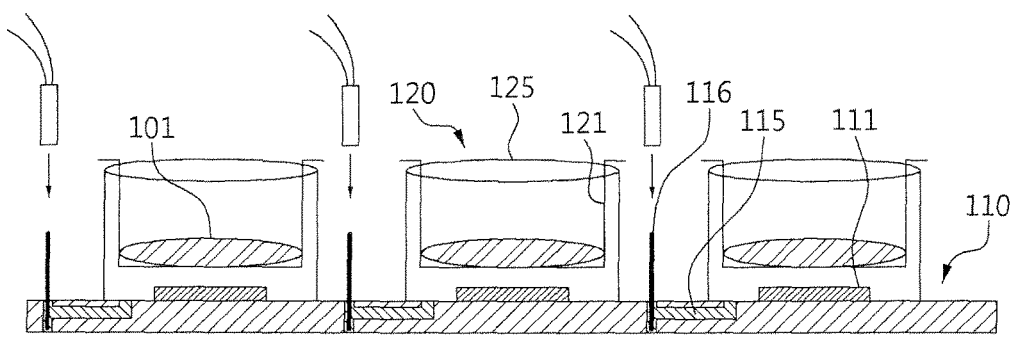
FIG. 2 is a diagram illustrating a cell stimulating system according to an embodiment of the present invention.
Figure 3:
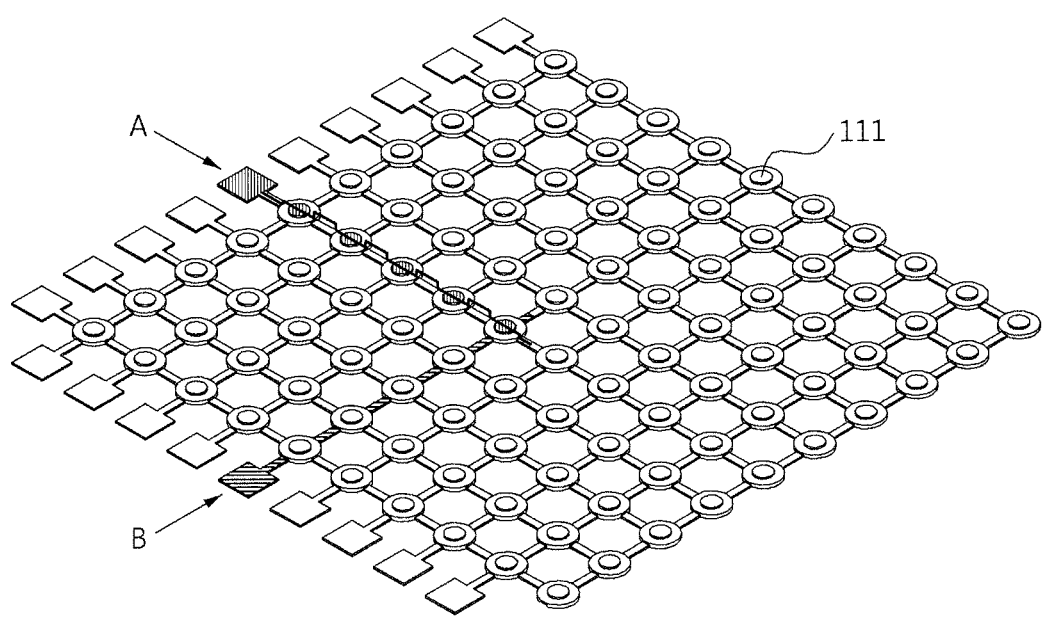
FIG. 3 is a diagram illustrating an operating principle of an oscillator of FIG. 2.
Figure 4:
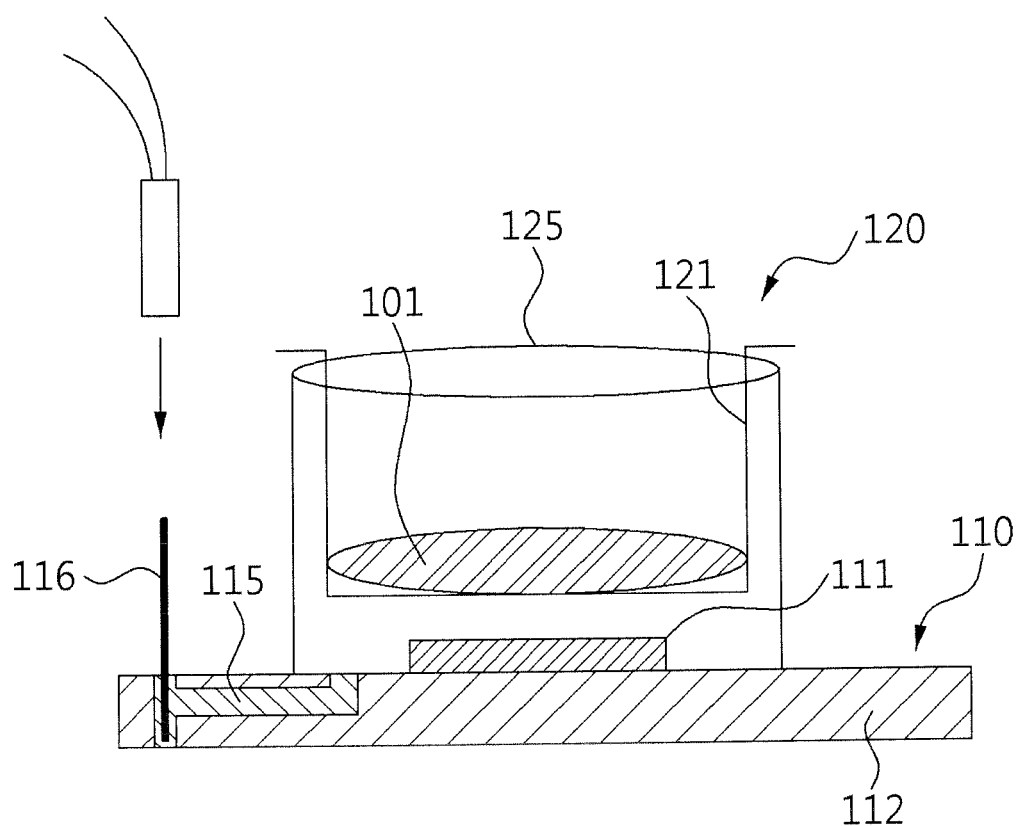
FIG. 4 is a diagram illustrating a cell container of FIG. 2.

FIG. 2 is a diagram illustrating a cell stimulating system according to an embodiment of the present invention, FIG. 3 is a diagram illustrating an operating principle of an oscillator of FIG. 2, and FIG. 4 is a diagram illustrating a cell container of FIG. 2.

Referring to FIG. 2, a cell stimulating system 100 includes an oscillator 110, in an integral ultrasound probe array type, including a plurality of ultrasound devices including an ultrasound device 111, having piezoelectric devices of piezoelectric materials, a plurality of cell containers including a cell container 120, configured to contain cells including a cell 101 that are selectively stimulated by the ultrasound devices including the ultrasound device 111, the cell container 120 being disposed on a top of each of the ultrasound devices including the ultrasound device 111, and a device operator (not shown) configured to operate the ultrasound device 111 selected from among the ultrasound devices.

The oscillator 110 may be provided in the integral ultrasound probe array type. The oscillator 110 may be produced using a micro electro mechanical system (MEMS), and the ultrasound devices including the ultrasound device 111 included in the oscillator 110 may be selectively operated based on a top-crossover-to-bottom method, as illustrated in FIG. 3.

As will be described later, each of the cell containers including the cell container 120 is disposed on the top of each of the ultrasound devices including the ultrasound device 111. It is possible to stimulate the cell 101 of the cell container 120 based on the top-crossover-to-bottom method and apply a plurality of variables (parameters) to the oscillator 110. However, an operating method of the ultrasound devices including the ultrasound device 111 is not limited to the aforementioned method. A method that operates the ultrasound device 111 selected from among the ultrasound devices including the ultrasound device 111 is also applicable.

In addition, the oscillator 110 may apply an electric energy of a predetermined frequency using a piezoelectric material and generate an ultrasound wave by vibration of the piezoelectric material. Because the generated ultrasound wave is a stimulus which is harmless to a human body unlike the electric energy or radiation used for the human body or the cell 101, the ultrasound wave may be the most appropriate stimulus for stimulating the cell 101.

Referring to FIG. 3, the ultrasound devices including the ultrasound device 111 of the oscillator 110 may be provided in a circuit structure in which the ultrasound devices are regularly arranged in a vertical direction and a horizontal direction. An alternating current (AC) voltage having a resonance frequency of the ultrasound device 111 may be applied to circuits formed in one direction, for example, a horizontal direction (a direction of an arrow A), of the oscillator 110, and the ultrasound devices disposed in another direction, for example, a vertical direction (a direction of an arrow B) may be used as grounds, such that the desired ultrasound device 111 may be selectively used. The AC voltage may be applied to the ultrasound device 111 selected based on the circuit structure and thus, stimulation to the cell 101 may be controlled by applying the selected AC voltage to the cell container 120 corresponding to the ultrasound device 111.

Referring to FIG. 4, the oscillator 110 includes a printed circuit board 112 on which the ultrasound devices including the ultrasound device 111 are regularly disposed in a vertical direction and a horizontal direction, and an electrode 115 configured to transmit a current applied from the device operator to the ultrasound device 111, and the electrode 115 is included in the printed circuit board 112 to correspond to the ultrasound device 111. A pin header 116 is provided to the electrode 115, such that the ultrasound devices may be selectively connected to the device operator and the ultrasound devices may be connected to another apparatus as necessary.

Although it is described that the ultrasound devices including the ultrasound device 111 are regularly disposed in the vertical direction and the horizontal direction, the way (*how**the manner in which the ultrasound devices are disposed is not limited thereto. The ultrasound devices may be disposed, for example, in a circular shape.

Although not illustrated in drawings, the device operator selectively operates the ultrasound devices including the ultrasound device 111 of the oscillator 110. As described above, the device operator may apply the AC voltage to the ultrasound devices disposed in one direction of the oscillator and use the ultrasound devices disposed in another direction as the grounds. Accordingly, the stimulation to the cell 101 may be controlled by changing a frequency of an ultrasound wave and an availability rate through the ultrasound devices including the ultrasound device 111.

As illustrated in FIGS. 2 and 4, the cell container 120 is disposed on a top of each of the ultrasound devices including the ultrasound device 111, such that the cell is stimulated by the corresponding ultrasound device 111. The cell container 120 may include a cell culture dish 121 configured to contain the cell 101 and a dish holder 125 configured to hold the cell culture dish 121 disposed on the top of the ultrasound device 111.

The dish holder 125 forms a space that contains the cell culture dish 121, and as illustrated in FIG. 4, the dish holder 125 is formed to have an open bottom. That is, the dish holder 125 may be bottomless.

As described in Background Art, the related art may have a limitation with respect to accurately estimating an intensity of an ultrasound wave to be used for stimulating the cell 101 because the intensity of the ultrasound wave provided from the ultrasound device 111 being transmitted is decreased due to a thick base of a configuration corresponding to the dish holder 125 according to an embodiment.

However, the dish holder 125 is bottomless such that the intensity of the ultrasound wave to be used for stimulating the cell 101 is not decreased. Thus, the intensity of the ultrasound wave may be accurately estimated.

As illustrated in FIG. 4, the cell culture dish 121 is inserted through the open top of the dish holder 125, such that the cell culture dish 121 hangs on the top of the holder. The cell culture dish 121 may be provided in a shape of an open ended rectangle with each end bent outwards. The bent ends may be hung on the top of the dish holder 125.

As illustrated in FIG. 4, the bottom of the cell culture dish 121 is adjacent to the ultrasound device 111, such that the bottom of the cell culture dish 121 is nearly in contact with the ultrasound device 111. Thus, the ultrasound wave generated from the ultrasound device 111 may stimulate the cell 101 of the cell culture dish 121. That is, the cell 101 is stimulated and an intensity of the ultrasound wave is not decreased.

Although not illustrated, the cell container 120 may be combined to a frame (not shown) having a space corresponding to a shape of the cell container 120 in a vertical direction and a horizontal direction. The frame disposed on the top of the oscillator 110, the cell container 120 put in the space formed in the frame, with a cover of the frame closed, forms the closed cell stimulating system 100, that is, an incubator system.

Hereinafter, descriptions of an ultrasound wave having a plurality of variables being transmitted to the cell containers including the cell container 120 through the oscillator 110 will be provided with reference to FIG. 5.

Figure 5:
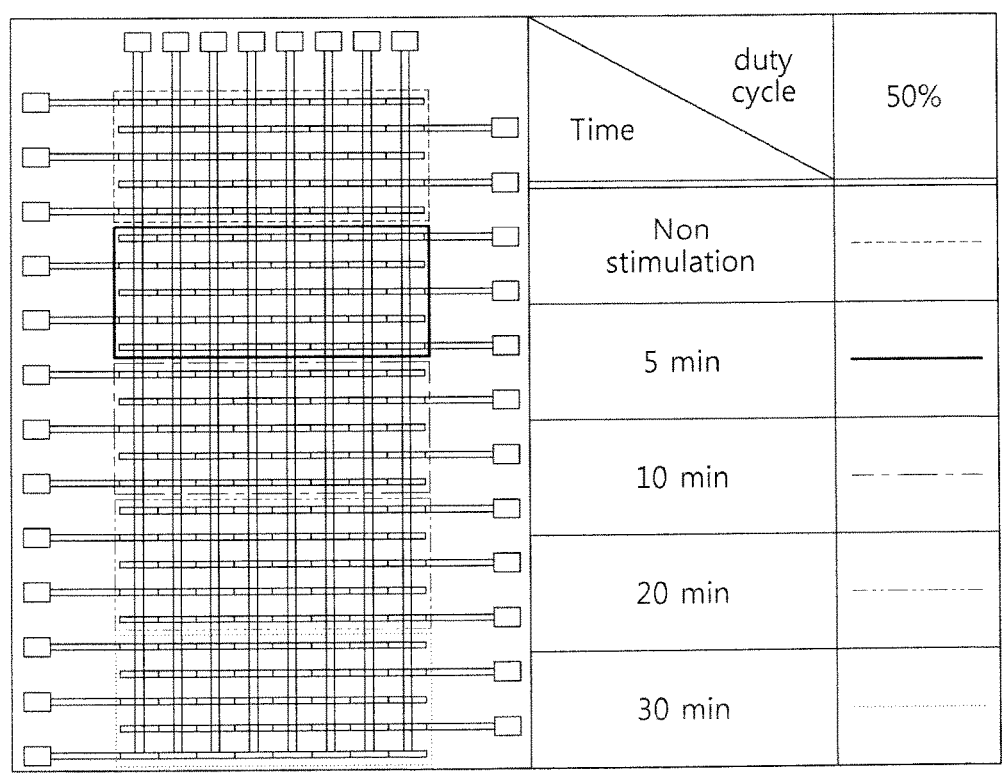
FIG. 5 is a diagram illustrating an example in which a cell stimulating system of FIG. 2 operates a plurality of variables in an oscillator.

FIG. 5 is a diagram illustrating an example in which a cell stimulating system of FIG. 2 operates a plurality of variables in an oscillator.

As illustrated, the oscillator 110 may have a plurality of intervals, and each interval may be adjusted based on a duty cycle or different cycles. The device operator may not stimulate a cell by adjusting each interval based on a 50% duty cycle, or stimulate the cell based on a 5-minute cycle, a 10-minute cycle, a 20-minute cycle, and a 30-minute cycle.

Thus, the present invention may selectively and simultaneously stimulate the cell 101 of the cell container 120 based on a plurality of parameters by selective operation of a plurality of ultrasound devices including the ultrasound device 111 by a device operator such that various experiments are simultaneously performed while cost and an amount of time used for the experiments are reduced.

The cell stimulating system 100 may use an oscillator to which a micro electro mechanical system (MEMS) is applied such that a size of an apparatus is minimized when compared to that of a related system, wherein an experiment of the cell 101 is performed in an incubator thereby increasing a reliability of the experiment.

Also, the present invention may enable an experimenter to perform an experiment based on a desired intensity of an ultrasound wave in a structure in which the cell container 120 transmits the ultrasound wave and an intensity of the ultrasound wave is not decreased.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

The invention claimed is:

1. A cell stimulating system, comprising:
an oscillator, in an ultrasound probe array type, including a plurality of ultrasound devices disposed in a matrix structure, the oscillator being produced using a micro electro mechanical system (MEMS);
a plurality of cell containers configured to each contain a cell that is selectively stimulated by the ultrasound devices, the cell containers being disposed on a top of the oscillator to correspond to each of the ultrasound devices; and
a device operator configured to operate an ultrasound device selected from among the ultrasound devices, wherein the device operator is configured to change the frequency of a wave of the ultrasound devices; and
wherein the device operator is configured to selectively operate the plurality of ultrasound devices such that an alternating current (AC) voltage having a resonance frequency of each of the plurality of ultrasound devices is applied to ultrasound devices disposed in one direction of the oscillator, and ultrasound devices disposed in another direction of the oscillator are used as grounds.

2. The system of claim 1, wherein the ultrasound devices are arranged in a polygonal shape.

3. The system of claim 1, wherein the oscillator includes:
a printed circuit board on which the ultrasound devices are disposed; and an electrode configured to transmit a current to be applied to each of the ultrasound devices, the electrode being included in the printed circuit board to correspond to each of the ultrasound devices.

4. The system of claim 1, wherein each of the cell containers includes:
a cell culture dish configured to contain the cell, the cell culture dish being disposed on a top of each of the ultrasound devices; and
a dish holder configured to hold the cell culture dish such that a bottom of the cell culture dish is adjacent to each of the ultrasound devices.

5. The system of claim 4, wherein the cell culture dish hangs on a top of the dish holder such that the cell culture dish is disposed on the top of each of the ultrasound devices.

6. The system of claim 4, wherein the dish holder is formed to have an open bottom such that the cell culture dish is in contact with each of the ultrasound devices.

7. The system of claim 1, wherein the cell of each of the cell containers is selectively and simultaneously stimulated based on a plurality of parameters, by selective operation of the ultrasound devices of the oscillator by the device operator.

* * * * *